United States Patent
Liao et al.

(10) Patent No.: US 9,102,895 B2
(45) Date of Patent: Aug. 11, 2015

(54) DETERGENT FOR LUBRICANT OIL AND PRODUCTION PROCESS THEREOF

(75) Inventors: Jinqing Liao, Wuxi (CN); Zhengming Shi, Wuxi (CN)

(73) Assignee: Wuxi South Petroleum Additive Co., Ltd., Wuxi, Jiangsu (CN)

( * ) Notice: Subject to any disclaimer, the term of this patent is extended or adjusted under 35 U.S.C. 154(b) by 0 days.

(21) Appl. No.: 13/519,064

(22) PCT Filed: Oct. 26, 2011

(86) PCT No.: PCT/CN2011/081332
§ 371 (c)(1),
(2), (4) Date: Jun. 25, 2012

(87) PCT Pub. No.: WO2012/167530
PCT Pub. Date: Dec. 13, 2012

(65) Prior Publication Data
US 2014/0113846 A1 Apr. 24, 2014

(30) Foreign Application Priority Data
Jun. 9, 2011 (CN) .......................... 2011 1 0153256

(51) Int. Cl.
*C10M 159/20* (2006.01)
*C10M 159/22* (2006.01)
*C10M 177/00* (2006.01)

(52) U.S. Cl.
CPC ........... *C10M 159/20* (2013.01); *C10M 159/22* (2013.01); *C10M 177/00* (2013.01); *C10M 2207/262* (2013.01); *C10N 2220/022* (2013.01); *C10N 2230/52* (2013.01); *C10N 2270/00* (2013.01)

(58) Field of Classification Search
CPC .................... C10M 159/20; C10M 2207/262; C10M 2207/2623; C10M 2207/2626
USPC ........................................................ 508/460
See application file for complete search history.

(56) References Cited

U.S. PATENT DOCUMENTS

| | | | |
|---|---|---|---|
| 1,998,750 A | 4/1935 | Bruson | |
| 3,372,116 A * | 3/1968 | Meinhardt | 508/460 |
| 4,810,398 A | 3/1989 | Van Kruchten et al. | |
| 4,869,837 A | 9/1989 | van Wijngaarden et al. | |
| 4,876,020 A | 10/1989 | Zon et al. | |
| 5,049,685 A | 9/1991 | Saito | |
| 5,281,345 A * | 1/1994 | Crawford et al. | 508/394 |
| 5,415,792 A * | 5/1995 | Campbell | 508/459 |
| 5,433,871 A * | 7/1995 | O'Connor et al. | 508/331 |
| 5,434,293 A | 7/1995 | Campbell | |
| 5,437,803 A * | 8/1995 | Cane et al. | 508/331 |
| 5,451,331 A | 9/1995 | O'Connor et al. | |
| 5,458,790 A | 10/1995 | Cane et al. | |
| 5,652,203 A * | 7/1997 | Asamori et al. | 508/460 |
| 5,734,078 A | 3/1998 | Feilden et al. | |
| 5,792,735 A | 8/1998 | Cook et al. | |
| 5,859,267 A | 1/1999 | Khattar et al. | |
| 6,034,039 A | 3/2000 | Gomes et al. | |
| 6,200,936 B1 | 3/2001 | Moreton | |
| 6,348,438 B1 | 2/2002 | Le Coent et al. | |
| 6,596,038 B1 | 7/2003 | Moreton et al. | |
| 6,599,867 B2 | 7/2003 | Hammond et al. | |
| 6,802,874 B2 | 10/2004 | Moreton et al. | |
| 7,009,072 B2 | 3/2006 | Muir | |
| 7,045,654 B2 | 5/2006 | Hobbs | |
| 7,087,557 B2 | 8/2006 | Muir et al. | |
| 7,456,136 B2 | 11/2008 | Moreton et al. | |
| 7,935,664 B2 * | 5/2011 | Dowding et al. | 508/460 |
| 7,960,324 B2 * | 6/2011 | Le Coent et al. | 508/460 |
| 8,012,918 B2 * | 9/2011 | Bertram et al. | 508/460 |
| 8,030,258 B2 * | 10/2011 | Le Coent | 508/460 |
| 8,404,627 B2 * | 3/2013 | Bertram et al. | 510/185 |
| 8,765,649 B2 * | 7/2014 | Yagashita | 508/460 |
| 8,778,856 B2 * | 7/2014 | Campbell et al. | 508/460 |
| 2004/0097750 A1 | 5/2004 | Muir et al. | |
| 2009/0170737 A1 * | 7/2009 | Campbell et al. | 508/460 |

FOREIGN PATENT DOCUMENTS

| | | |
|---|---|---|
| CN | 1144216 | 3/1997 |
| CN | 1671829 | 9/2005 |
| CN | 1708471 | 12/2005 |
| EP | 0248465 | 12/1987 |

* cited by examiner

*Primary Examiner* — Ellen McAvoy
(74) *Attorney, Agent, or Firm* — Greer, Burns & Crain, Ltd.

(57) ABSTRACT

A lubricant oil detergent and a producing process thereof are disclosed. A process for producing a lubricant oil additive having a TBN from about 100 to about 400 includes reacting, at an elevated temperature, of composition (A) an alkyl salicylic acid or an alkyl salicylate ester, composition (B) an alkaline earth metal hydroxide added by one time or plural times during the reaction; composition (C) which contains at least one compound which is (i) an alcohol, or (ii) an carboxylic acid or an carboxylic anhydride; composition (D) base oil; and composition (E) carbon dioxide introduced after the composition (B) by one time, or introduced each time when the composition (B) is added if the composition (B) is added by plural times; solvent having a low boiling point is removed from the reacted mixture after the overbasing under vacuum, and the reacted mixture is filtered to obtain a clear liquid product.

6 Claims, No Drawings

DETERGENT FOR LUBRICANT OIL AND PRODUCTION PROCESS THEREOF

FIELD OF THE INVENTION

The present disclosure relates to an additive used for producing lubricant oil and a production process thereof, particularly to an alkaline earth cleaner with high alkaline for lubricant oil and a production process thereof, and more particularly to a detergent for lubricant oil and a production process thereof.

BACKGROUND OF THE INVENTION

To provide lubricant oil with a certain new feature or improved existing features during the production of the lubricant oil, various additives such as an extreme pressure additive, a detergent, a dispersant, an antioxidant and a tackifier are usually added to the base oil of the lubricant oil. The detergent, among the numerous additives for lubricant oil, is widely used for various purposes and is present at a significant ratio among the additives for lubricant oil.

The detergent is a substance with a surface activity, which is capable of absorbing solid particle contaminants in the lubricant oil and enabling such contaminants to suspend at the surface of the lubricant oil, in order to ensure clear lubricant oil is used for lubricating cycles and to avoid the resulting high temperature and paint film, thereby enabling any insoluble substance such as jellies and carbon deposition resulting from the oxidation of the lubricant oil to be suspended in the lubricant oil at a colloidal state without being deposited on any parts of an engine, or enabling the lubricant oil to clean off the jellies and carbon deposition deposited on the parts of the engine through its cleaning effect. The detergent of the substance described above is also referred to as a detergence dispersant because the dispersant role of the substance.

For example, the presently available detergents for lubricant oil comprise a synthetic calcium alkyl benzene sulfonate having a low base value, a linear synthetic calcium alkyl benzene sulfonate having a high base value, a long-chain linear alkyl benzene synthetic calcium sulfonate having a high base value, a synthetic calcium dialkyl benzene sulphonate having a high base value, a long-chain linear alkyl benzene synthetic magnesium sulfonate having a high base value, a sulfurized calcium alkyl phenolate having a high base value, polyisobutenyl succinimide, polyisobutenyl succinimide boride, polyisobutenyl succinimide having a high molecular weight, and polyisobutenyl succinimide boride having a high molecular weight.

In the prior art, it is known to adopt a compound of alkaline earth metal salt of organic carboxylic acid as the additive for the lubricant oil. The alkaline earth metal salt of organic carboxylic acid is characterized by its dispersancy which facilitates to keep the interior of the cylinder of the engine clean and eliminates the carbon deposition on the piston and piston grooves, thereby avoiding the piston ring sticking. Therefore, the alkaline earth metal salt of organic carboxylic acid can be used as the detergent (or the detergence dispersant) for lubricant oil.

The process for preparing the alkaline earth metal salt or overbased alkaline earth metal salt of organic acid is also known. Due to the alkalinity reserve provided by the overbasing, when used as a composition of the lubricant oil, the alkaline earth metal salt or overbased alkaline earth metal salt of organic acid can neutralize acidic compound generated during the operation of an engine. Therefore, any potential sludge is dispersed due to the dispersibility of the organic acidic alkaline earth metal salt, thereby accelerating the neutralization of acidic matters generated by the sludge.

A salicylic acid with high alkaline may be prepared by overbasing the corresponding alkyl salicylic acid or alkyl salicylate methyl ester. The alkyl group generally contains a long-chain alkyl with more than about 14 carbon atoms to achieve sufficient oil solubility. A traditional method for preparing the alkyl salicylic acid includes: alkylating a phenol to obtain an alkyl phenol; and carbonating the alkyl phenol by the Kolbe-Schmitt reaction to obtain the alkyl salicylic acid. Alternatively, the alkyl salicylic acid may be prepared by directly alkylating a salicylic acid or salicylate methyl ester with α-olefin using a catalyst such as a sulphuric acid, a methanesulfonic acid, and emathlite.

U.S. Pat. No. 1,998,750 A disclosed that a salicylic acid is condensed with any nonaromatic monohydric alcohol having from 5 to 7 carbon atoms, or with compounds capable of furnishing a pentyl group, a hexyl group, a cyclohexyl group, or a heptyl group at the presence of a Sulfuric Acid, to generate an alkyl salicylic acid.

U.S. Pat. No. 3,372,116 A discloses a method for preparing an alkaline salicylate, including reacting, at a temperature between about 25° C. and the reflux temperature, (A) a hydrocarbon-substituted phenol or a substantially neutral alkali metal salicylate or alkaline earth metal salicylate salt, (B) about 1-10 equivalents, per equivalent of (A), of a calcium or strontium base, and (C) carbon dioxide, in the presence of about 0.002-0.2 equivalent, per equivalent of calcium or strontium base, of a carboxylic acid having up to about 100 carbon atoms or an alkali metal, alkaline earth metal, to obtain the alkaline salicylate.

U.S. Pat. No. 4,810,398 A disclosed a process for the preparation of basic alkaline earth metal salts of a blend of organic carboxylic acid, which includes: (a) preparing a mixture of one equivalent of the blend of organic carboxylic acids and more than one equivalent amount of an alkaline earth metal hydroxide and/or oxide in a hydrocarbon solvent; (b) introducing carbon dioxide into the mixture obtained in an amount of at least 0.5 equivalent carbon dioxide per equivalent of excess alkaline earth metal; and (c) removing residual solids, if any, and an aqueous layer, if any. The blend of organic carboxylic acids comprise a $C_{8-30}$ alkyl salicylic acid and one or more alkane carboxylic acids in which the alkyl moiety is branched and has from 4 to 40 carbon atoms. Such a salt has dispersant properties and is suitable for use in lubricating oil and fuel compositions.

U.S. Pat. No. 4,869,837 A disclosed a process for the preparation of a basic alkaline earth metal salts of a blend of organic carboxylic acids, including: (a) preparing a mixture of one equivalent of the blend of organic carboxylic acids and more than one equivalent of an alkaline earth metal hydroxide and/or oxide in a hydrocarbon solvent; (b) introducing carbon dioxide into the mixture obtained in an amount of at least 0.5 equivalent carbon dioxide per equivalent of excess alkaline earth metal; and (c) removing residual solids, if any, and an aqueous layer, if any, whereby. The blend of organic carboxylic acids comprises an oil-soluble alkyl salicylic acid and one or more hydrocarbon substituted succinic acids or anhydrides, in which the hydrocarbon radical has a number average molecular weight from 120 to 5000.

U.S. Pat. No. 4,876,020 A disclosed a lubricating oil formula, including a lubricating base oil, one or more overbased alkaline earth metal salts of an aromatic carboxylic acid, and a stabilizing agent which has been selected from a polyalkoxylated alcohol having a molecular weight from 150 to 1500.

U.S. Pat. No. 5,049,685 A disclosed a substituted salicylic acids and salts thereof that have good solubility in water, organic solvent or organic polymeric. The substituted salicylic acids and salts thereof are very favorable as bactericidal germicidal agents, stabilizers for polymeric compounds or color developing agents for recording materials.

U.S. Pat. No. 5,415,792 A disclosed overbased alkyl salicylate which are useful additives for lubricant oil compositions. The overbased alkyl salicylate compositions impart detergency and disperancy to the lubricant oil composition as well as provide for alkalinity reserve.

U.S. Pat. No. 5,434,293 A disclosed is a method for alkylating alkyl salicylate using a solid acidic alkylation catalyst and approximately equimolar amounts of alkyl salicylate and alkylating feedstock.

U.S. Pat. No. 5,451,331 A disclosed a process for the production of a lubricating oil additive having a TBN greater than 300. The process includes reacting, at elevated temperature, an alkyl salicylic acid, alkaline earth metal base, a lubricating oil, a carbon dioxide, and an alcohol. The process necessarily utilize inorganic halide or ammonium alkanoate.

U.S. Pat. No. 5,458,790 A disclosed an additive concentrate having a TBN greater than 300 for incorporation into a finished lubricating oil. The additive concentrate comprises a lubricant oil and a lubricating oil soluble overbased alkaline earth metal hydrocarbyl salicylate modified by reaction, which mainly includes: (a) an aldehyde, and (b) from 2 to 40% by weight, based on the weight of the concentrate, of either (i) a carboxylic acid, or (ii) a di- or poly-carboxylic acid containing from 36 to 100 carbon atoms or an acid anhydride, acid chloride or ester thereof.

U.S. Pat. No. 5,652,203 A disclosed a process for the preparation of a lubricating oil additive. In the process, an aromatic carboxylic ester is subjected to ring alkylation with an olefin, reacted with the oxide or hydroxide or an alcoholate of a divalent metal and carbon dioxide with the removal of formed water and/or an alcohol from the reaction mixture. The lubricating oil additive provides excellent oxidation stability, low susceptibility to carbonization and cleanability as compared with the conventional, commercially-available additives.

U.S. Pat. No. 5,734,078 A disclosed a process for the production of an alkyl salicylic acid, in which the alkyl substituent has at least 6 carbon atoms, comprising reacting salicylic acid with an olefin having at least 6 carbon atoms at elevated temperature in the presence of sulphuric acid as a catalyst. The alkyl salicylic acid is overbased at temperature from 50 to 100° C. in the presence of an organic solvent.

U.S. Pat. No. 5,792,735 disclosed a lubricating oil composition suitable for use in low or medium speed diesel engines, which comprises a fuel oil, a hydrocarbyl-substituted phenate, and at least one of a hydrocarbyl-substituted salicylate and a hydrocarbyl-substituted sulphonate. The hydrocarbyl-substituted phenate is preferably one modified by incorporation of a carboxylic acid of formula $RCH(R_1)CO_2H$, where R is $C_{10}$-$C_{24}$ alkyl group, and $R_1$ is hydrogen or a $C_1$-$C_4$ alkyl group, e.g. stearic acid.

U.S. Pat. No. 6,034,039 A disclosed complex detergents that provide improved deposit control and corrosion protection in crankcase lubricants. The lubricating oil composition comprises a mixture of at least two metal-containing detergents, a first detergent (a), being a metal phenate, sulphonate, salicylate, naphthenate, or carboxylate, and a second, detergent (b), being a calcium overbased detergent comprising a surfactant system derived from at least two surfactants, at least one of which is a sulphurized or non-sulphurized phenol or a derivative thereof and the other, or at least one other, of which is a surfactant other than a phenol surfactant, the proportion, as measured, of the phenol in the surfactant system being at least 45 mass %, and the overbased detergent having a TBN: % surfactant ratio of at least 14, advantageously at least 15, especially at least 19.

U.S. Pat. No. 6,200,936 A disclosed a process for the preparation of salicylization arene and its overbased product, and its use as a lubricating oil additive.

U.S. Pat. No. 6,348,438 A disclosed that an overbased alkaline earth metal single-aromatic ring hydrocarbyl salicylate-carboxylate is produced by overbasing a mixture of a single-aromatic ring hydrocarbyl salicylate, at least one solvent, a metal hydroxide, and an alkyl polyhydric alcohol alkaline earth metal hydroxide, by contacting that mixture with carbon dioxide under overbasing reaction conditions. The alkyl group of the alkyl polyhydric alcohol has from one to five carbon atoms. The overbased metal single-aromatic ring hydrocarbyl salicylate is treated, before, during, or subsequent to overbasing, with a long-chain carboxylic acid to form a single-aromatic ring hydrocarbyl salicylate-carboxylate.

U.S. Pat. Nos. 6,596,038 A and 6,802,874 A disclosed linear compounds in the form of oligomers or polymers, containing unsubstituted or substituted phenol units and unsubstituted or substituted salicylic acid units, and a synthesis process of the compounds. These compounds are useful as additives for lubricants and fuels. Metal salts of these compounds are useful as lubricant additives.

U.S. Pat. No. 6,599,867 A disclosed overbased detergent additives for lubricating oils which comprise an organic substantially aromatic carboxylate, such as an alkyl salicylate, as a surfactant, and have a TBN of 200 or greater, an active ingredient content of 70 mass % or greater, a kinematic viscosity at 100 DEG C. of less than 1000 mm2s-1 and a basicity index (BI) of less than 13.

U.S. Pat. No. 7,009,072 A disclosed that the alkylation of a salicylic acid is conducted using C14 or greater linear alpha-olefins to produce oil soluble alkyl salicylic acids. The oil soluble alkyl salicylic acids are subsequently neutralized and overbased by carbonation of lime using CO2 in the presence of a promoter, such as methanol, and a surfactant, e.g., alkyl salicylic acid. The reaction mixture after overbasing is filtered and solvents are removed by distillation.

U.S. Pat. No. 7,045,654 A disclosed a process for the production of alkyl salicylic acids. The process comprises reacting a salicylic acid with an olefin having at least four carbon atoms at elevated temperature in the presence of a perfluoroalkylsulfonic acid, an alkylsulfonic acid, or an acidic clay as a catalyst.

U.S. Pat. No. 7,087,557 A disclosed a Styrenated salicylate, which has an anti-oxidant property, for use as a metal based detergent additive. In the presence of methanol as a promoter, the Styrenated salicylate is neutralized and overbased to result in the overbased Styrenated calcium or magnesium salicylate.

U.S. Pat. No. 7,456,136 A disclosed a linear compound and a metal salt or boron-containing metal salt thereof, which contains one or more carboxyl-containing phenol units or derivatives thereof and one or more on average at least C18 hydrocarbyl-substituted hydroxyaromatic units or derivatives thereof connected by one or more divalent bridging groups. A concentrate contains the linear compound or metal salt thereof and an organic diluent is further disclosed. In addition, a lubricating oil composition contains a minor amount of the linear compound or metal salt thereof and a major amount of a lubricating base oil is disclosed.

Although the above detergents for lubricant oil are disclosed in the prior art, inorganic halide or ammonium alkanoate is required during the preparation of such detergents, and a hydrocarbon solvent is necessary during the preparation, resulting a high residual carbon value.

SUMMARY OF THE INVENTION

In view of the drawbacks in the prior art, the present disclosure provides an alkaline earth metal alkyl salicylate used for lubricant oil and a production process thereof.

To prepare the alkaline earth metal alkyl salicylate of the present disclosure, an oil soluble alkyl salicylic acid or alkyl salicylate is used and added as a material into a mineral oil diluent (SN 150), to which CaO of an approximately equal equivalent weight is added, and then the resultant mixture is heated to 120° C., at which a glycol is dripped slowly to the mixture to neutralize the alkyl salicylic acid with stirring. Subsequently, a dried nitrogen gas is flowed to remove the generated water from the reactants. Then, more CaO and glycol may be added in batches while a carbon dioxide gas is flowed in.

For example, an alkyl salicylic acid or an alkyl salicylate ester that is of a particular formula (I) below prior to its neutralizing or overbasing is used in the present disclosure,

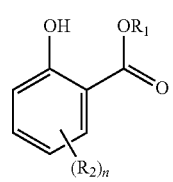

(I)

where $R_1$ represents a hydrogen or an alkyl group including 1 to 3 carbon atoms, $R_2$ represents an alkyl group including 10 to 50 carbon atoms, and n is 1 or 2.

In another aspect, the present application provides a process for producing an alkaline earth metal salicylate, including steps of:

A) neutralizing an oil soluble alkyl salicylic acid or alkyl salicylate ester;

B) at a temperature from 120° C. to 180° C., flowing a carbon dioxide gas into the neutralized oil soluble alkyl salicylic acid or alkyl salicylate ester obtained from step A) that is added with a glycol and an optional arboxylic acid or carboxylic anhydride, to overbase the oil soluble alkyl salicylic acid or alkyl salicylate ester;

C) filtering the product from step B); and

D) partial of the diluent is removed from the product of step C) by vacuum distillation, as required, for the purpose of further concentrating.

In contrary to the prior art, the process for producing the alkaline earth metal alkyl salicylate of the present application does not utilize an inorganic halide and an ammonium alkanoate, and a hydrocarbon solvent is not necessary during the production.

In the production process of the present application, an oil soluble alkyl salicylic acid or alkyl salicylate methyl ester is used as material, and the oil soluble alkyl salicylic acid is preferable. The alkyl salicylic acid may be obtained from the Kolbe-Schmitt reaction route, or from the direct alkylation of a salicylic acid and an olefin. The oil soluble alkyl salicylic acid may include more than one, for example two or three, substituted alkyl. The substituted alkyl includes at least 12, preferably 14 to 30 carbon atoms. If the alkyl salicylic acid includes merely one alkyl substituent, the alkyl substituent preferably includes 14 to 26 carbon atoms. The alkyl substituent may be a linear chain or a branched chain, and preferably a linear chain. The suitable olefin may include, but not limited to, 1-tetradecene, 1-hexadecylene, 1-octadecene, 1-icosene, 1-docosene, 1-tetracosene and mixture thereof.

An oil soluble alkyl salicylic acid is mixed with a mineral oil diluent (SN 150), to which CaO of an approximately equal equivalent amount is then added, then the resultant mixture is heated to 120° C. with stirring and the alkyl salicylic acid is neutralized. A glycol is dripped to the mixture at a temperature between 120° C. and 180° C., while a dried nitrogen gas is flowed into the mixture to remove the generated water simultaneously. Then, more CaO and glycol may be added to the mixture while a carbon dioxide gas is flowed in for overbasing.

In another aspect, the present application provides a process for preparing or producing an alkaline earth metal salicylic acid, including steps below.

A) the oil soluble alkyl salicylic acid or alkyl salicylate ester, particularly alkyl salicylate methyl ester is neutralize with a base;

B) at a temperature from 120° C. to 180° C., a carbon dioxide gas is flowed into the product obtained from step A) above in the presence of the added glycol and an optional arboxylic acid or carboxylic anhydride, to overbase the oil soluble alkyl salicylic acid or alkyl salicylate ester;

C) filtering the product from step B) above; and

D) some of the diluent may is removed from the product of step C) above by further vacuum distillation, as required, for the purpose of further concentrating.

In contrary to the prior art, the process for preparing or producing the alkaline earth metal salicylic acid of the present application does not utilize an inorganic halide and an ammonium alkanoate, and a hydrocarbon solvent is not necessary during the production.

In a further aspect, the present application provides an alkaline earth metal alkyl salicylate detergent prepared with the process of the application, including a calcium alkyl salicylate detergent, a magnesium alkyl salicylate detergent or the mixture thereof.

In the preparation process of the application, sufficient base is added to obtain the overbased salt, that is, a ratio of the equivalent weight of metal hydroxid to that of the alkyl salicylic acid is typically larger than 1.2, or even larger than 10 or more.

The overbased alkaline earth metal alkyl salicylate of the application may be obtained by overbasing a neutral alkaline earth metal alkyl salicylate, resulting in an alkaline earth metal carbonate such as a calcium carbonate and a magnesium carbonate, or an alkaline earth metal borate such as magnesium borate.

The base number of the alkyl salicylate detergent is not limited. Typically, the total base number of the alkyl salicylate detergent is in a range of 100 to 400, preferably 150 to 350 milligrams of potassium hydroxide per gram.

In the preparation process of the present application, the glycol may be added by one time or several times during the reaction.

In the preparation process of the present application, the metal hydroxide may be added by one time or several times during the reaction.

Preferably, a hydrocarbon solvent is not used in the preparation process of the present application. However, an inert hydrocarbon solvent, which may be of a fatty group or an aromatic group, may be used in the preparation process. Suitable examples of the inert hydrocarbon solvents include a dimethylbenzene, a naphtha, an aliphatic alkane and an aliphatic cycloalkane.

For the purpose of using the overbased alkyl salicylate as an additive for lubricant oil, base oil is preferably contained as a diluent. The base oil may be animal oil, vegetable oil or mineral oil. The base oil may be derived from petroleum, and may be naphthene base oil, paraffin base oil or the mixed base oil. In addition, the lubricant oil may be synthetic oil such as synthetic ester lubricant oil or polyolefin lubricant oil, or semi synthetic oil.

The carbon dioxide used in the preparation process for the overbased alkyl salicylate may be of a solid form, or preferably a gas form so that the carbon dioxide may be blown into the reaction mixture. The carbon dioxide is typically introduced after the adding of the metal hydroxide.

In the preparation process of the present application, the calcium oxide is taken as the unique base repertory, and the calcium oxide used in the reaction mixture is of an amount which is designed so that the minimal excessive required total base number is achieved. Such a particularly designed amount of the calcium oxide results in that the reaction efficiency is high and there is almost no solid residuum after the reaction, thereby facilitating the filtering of the product. The limit of the amount of the used calcium oxide in the present application is advantageous over some other processes in the prior art. Among the processes in the prior art, for example, if methanol is used as a promoter and calcium oxide and calcium hydroxide are used as the base repertory, relatively more excessive metal hydroxide is required to achieve the high total base number and good filtering, as a result, a high amount of solid residuum is present after the reaction, which is disadvantageous for the subsequent processing.

Another advantage of the preparation process of the present application is that a metal halide catalyst is not necessary during the overbase process. However, it is also possible to use a catalyst, which may be an organic compound or preferably an inorganic compound, during the process for the overbase production of the overbased alkaline earth metal salts, if desired. Some of the suitable inorganic compounds are hydrogen halide, metal halide, ammonium halide, paraffinic acid metal salts, paraffinic acid ammonium salts, or mono-, di-, tri-, or tetra-alkyl ammonium formate, or paraffinic acid salts. Examples of the suitable catalysts are calcium chloride, ammonium chloride, calcium acetate, ammonium acetate, zinc acetate, tetramethyl ammonium acetate, and may be typically present at an amount of about 2% by weight.

Reaction temperature suitable for the process of the present application is of a range of about 50° C. to about 200° C., preferably about 100° C. to about 180° C., and more preferably about 120° C. to about 160° C., and the carbon dioxide is flown in for such a period of time that sufficient carbon dioxide is inputted to the reaction mixture to complete the reaction.

With the process of the application, the overbased alkyl salicylate obtained after the removal of glycol by vacuum distillation and the subsequent filtering does not contain any solvent. If desired, the overbased alkyl salicylate may be further distillated to remove some of the diluent oil so that the base number of the overbased alkyl salicylate may be improved over 400.

Generally, the process for preparing the overbased alkyl salicylate includes that an alkyl salicylic acid, along with an optional carboxylic acid or carboxylic anhydride or calcium sulfonate or a sulfonic acid (calcium compounds are taken as an example for the sake of description, while the process is likewise applicable to magnesium compounds and a mixture of calcium and magnesium, as appreciated by those skilled in the art) are reacted with calcium oxide or calcium hydroxide in the diluent oil, and the gas of carbon dioxide is introduced to the diluent oil, so that the excessive calcium carbonate is introduced to the alkyl salicylate, also to the calcium carbonate or the calcium carboxylate if they exist, thereby rendering the desired base value of the product. In such a process, the applicant found that the addition of an alcohol of a low molecular weight, especially the glycol, may facilitate the formation of very satisfying dispersed micelle by the calcium carboxylate at an elevated temperature.

A dispersant is optional for producing the overbased alkyl salicylate. One of the applicable dispersants is a product obtained from the reaction of an alkyl-substituted succinic acid or an anhydride with an amine containing at least one primary amine or secondary amine, such as a polyene polyamines. Here, an ammonia is another one of the applicable dispersants. A bi-succinamide dispersant may be used in the present invention. The bi-succinamide may be obtained by the reaction of an alkyl-substituted succinic acid or a succinic anhydride with an amine containing at least two prime and/or secondary nitrogens. The bi-succinamide may be, for example, a diamino-diene, a diethylene triamine, a triethylenetetramine or a tetren), and a bi-polyisobutylene succinamide of N-Tetramethyl dippropylene triamine (see U.S. Pat. No. 3,438,899 A by Benoit). The dispersants described above may be used separately or in combination.

The process for producing the additive for lubricant oil of a Total Base Number from about 100 to about 400 according to the invention is different in technology from that in the prior art. However, the amounts of materials used in the process of the invention may be the same as those of materials used in the process of the prior art, or may be particularly designed by those skilled in the art according to the reaction formula. The inventive aspect of the present invention does not lie in the amounts of materials used and therefore the amounts are not specially limited in the invention.

The detergent of the overbased calcium alkyl salicylate according to the present invention may be added into an engine or lubricant oil at an amount from about 0.1% to about 25% or more.

The present invention is applicable to various lubricant oils such as one or more natural oils, one or more synthetic oils or the mixture thereof. The nature oils may include an animal oil and a plant oil (such as a castor oil or a lard oil), a liquid petroleum, a refined hydrogenation oil, a paraffin mineral oil treated with a solution or acid, a naphthene base lubricant oil and a mixed paraffin oil. The base oil of a lubricant oil viscosity obtained from the coal or shale oil may also be applicable to the detergent of overbased calcium alkyl salicylate.

The synthetic lubricant oil includes hydrocarbon oil and halogen substituted hydrocarbon oil, e.g. olefin polymer such as polybutylene, polypropylene, polypropylene isobutene, Chlorinated Polybutylene, poly(1-hexene), poly(1-octene) or poly(1-decene); alkylbenzene such as dodecyl benzene, tetradecyl benzene, bi-nonyl benzene or bi(2-ethylhexyl)benzene; polyphenylene such as biphenyl, terphenyl or alkylation polyphenol; alkylation diphenyloxide; alkylation diphenylsulfide and derivatives thereof; analog and/or homologue of the above.

The esterification and/or etherification of an olefin oxidation polymer and terminal hydroxyl results in a modified derivative, which constitutes another known synthetic lubricant oil. A typical one of such polymers is a polyether polymer prepared from the polymerization of an ethylene oxide or a propylene oxide. Typical examples of such polyether polymer may include, but not limited to, a methyl poly isoallylalcohol ether of an average molecular weight of 1000, a poly glycol diphenylate of an average molecular weight of 500-1000, a poly propylene glycol ether of an average molecular weight of 1000-1500, or a mono-poly carboxylic ester such as acetate, mixed C3 to C8 fatty acid esters, and C13 oxyacid Tetraglycol diester.

Another suitable synthetic lubricant oil includes a dibasic acid ester such as a phthalic acid, a succinic acid, an alkyl succinic acid, an alkenyl succinic acid, a maleic acid, an azelaic acid, a suberic acid, a sebacic acid, a fumaric acid, an adipate, a Linoleic acid dimmers, a malonic acid, an alkyl malonic acid and/or an alkenyl malonic acid, and various esters of alcohol. Typical examples of the alcohol includes, but not limited to butanol, n-hexanol, dodecanol, 2-ethylhexanol, Ethylene Glycol, diethylene glycol mono ether and/or propylene glycol, and typical examples of the ester includes, but not limited to Dibutyl Adipate, Di(2-ethylhexyl)sebacate, Boletic acid dihexyl ester, dioctyl sebacate, Nonanedioic acid, Di-2-ethylhexyl azelate, dioctyl phthalate, decylphthalate, di-icosyl sebacate, and a complicated ester prepared from the reaction of a Linoleic acid diisooctyl ester dimmer, a sebacic acid of 1 mol, tetraglycol of 2 mol and a 2-ethyl hexoic acid of 2 mol.

Applicable synthetic ester oils include an ester produced from an mono carboxylic acid of C5 to C12, a polyol, and a polyol ether such as a pentanediol, a trimethylolpropane, a pentaerythritol, a di-pentaerythritol, and a tri-pentaerythritol.

Examples of another type of applicable synthetic lubricant oil include a silicon-based oil such as polyalkyl-, polyaryl-, polyalkoxy-, or polyaryloxy-siloxane oil and silicate oil, including tetraethyl silicate, tetra-isopropyl silicate, tetra-(2-ethyl-hexyl)silicate, tetra-(4-methyl-2-ethyl-hexyl)silicate, tetra-(p-tert-butyl-phenyl)silicate, hexa-(4-methyl-2-amoxy) disiloxane, poly(methyl)siloxane and poly(methylphenyl)siloxane. Some other synthetic lubricant oils include liquid esters prepared from phosphorus acids, such as tricresyl phosphate, trioctyl phosphate, 1-decyl diethyl phosphate, and a liquid macromolecular tetrahydrofuran ester.

The unrefined, refined or regenerated lubricant oil is also applicable for the present invention. The unrefined oil is lubricant oil directly from a natural or synthetic source without any further purification process. For example, the unrefined oil includes an oil shale-based oil directly obtained from an oil shale retorting plant, petroleum directly obtained from a petroleum distillation plant, or an ester directly obtained from the esterification process but not further processed. The refined oil is similar with the unrefined oil, except that the refined oil has been subjected to one or more additional purification processes such as distillation, solvent extraction, acid or base extraction, filtration, or diacolation that are well known in the art, to improve one or more of its properties. The regenerated oil is obtained similarly with the refined oil, but is applicable to the used oil. Such re-refined oil is called as regenerated oil or re-processed oil, which is usually obtained by removing the disabled additives and the decomposed oil through corresponding techniques.

The present invention is particularly suitable for engine oil formula or additives. Therefore, the term of engine oil used in the present invention refers to oil that may serve as engine lubricant oil, by way of example, including automobile oil or diesel engine oil. The compositions of the lubricant oil according to the present invention are also suitable for bunker oil, which may be used for a four-stroke diesel plunger engine and a two-stroke crosshead diesel engine, for example.

The viscosity of the lubricant oil prepared in the present invention shall be within the range of the conventional lubricant oil viscosity, which is typically from about 45 SUS to 6000 SUS at the temperature of 100° F. (about 38° C.). The lubricant oil further may contain one or more overbased alkaline earth metal detergent, at least one of which is the neutral or overbased alkyl salicylic acid containing metal described in the invention. The amount of the detergent is generally from 0.01% up to 20% by weight, preferably 0.1% to 10% by weight, and more preferably 0.1% to 5.0% by weight. The percentage by weight in the invention is relative to the weight of the entire lubricant oil, except where otherwise described.

The amount of additives in the finished lubricant oil depends on the intended usage properties. The bunker lubricant oil typically has a Total Base Number of 9 to 100, while the lubricant oil for automobile engine typically has a Total Base Number of 4 to 20.

The term "Total Base Number" or "TBN" used in the invention means the amount in milligram (mk) of the equivalent potassium hydroxide per one gram of the additive. Therefore, a higher Total Base Number means a higher basicity of the product, thereby obtaining a larger basicity scale. The Total Base Number of the additive may be easily measured by the ASTM test method No. D2896 or equivalents thereof.

The finished lubricant oil (i.e. a lubricant oil product) may further contain sufficient one or more traditional lubricant oil additives, such as a viscosity index improver, an antiwear additive, an antioxidant, a dispersant, a rust inhibitor or a pour point depressant.

DETAILED DESCRIPTION OF THE EMBODIMENTS

The alkyl salicylic acid may be prepared according to the second embodiment of U.S. Pat. No. 7,045,654 A. The method for preparing the alkyl salicylic acid is as follows.

A mixture of salicylic acid powder (which has a weight of 1100 kg, for example) and C14-C18 α-olefin (which has a weight of 1895 kg, for example) is added into a reactor of 6000 Liters (L) in which a mechanical stirrer and a reflux condenser are provided, and then is stirred at a rate of 250-300 rpm (Revolutions Per Minute), thereby obtaining a white suspension liquid. An anhydrous methanesulfonic acid (which has a weight of 232 kg, for example) is added to the obtained white suspension liquid at one time. The resultant product is heated with stirring under nitrogen protection to a temperature of 120° C. The suspension liquid turns into kermesinus along with the reaction, but the suspended matter disappears. The sublimated salicylic acid crystal is present at a cooler portion of the reactor. After resting at 120° C. for 24 hours, the reacted mixture is not heated but is cooled. With the use of light naphtha (which has a weight of 2995 kg, for example), the resulting product is transferred from the reactor to a sedimentation tank having a plastic internal lining, and then is subjected to sedimentation, to obtain an upper phase and a dark colored part containing the used acid catalyst. The upper phase is distillated to remove the solvent at a temperature of 90° C. under a vacuum having a pressure less than 10 millibars, thereby obtaining clear and nigger-brown oil without any solvent. The acid value of the alkyl salicylic acid obtained by the method above is about 136.

EXAMPLE 1

The obtained nigger-brown and oil soluble alkyl salicylic acid without any solvent, which has a weight of 168 grams, is added to a reaction container containing base oil of 78 grams and CaO of 16 grams, and the mixture is heated up to 120° C. with stirring. Glycol of 28 grams is added to the mixture slowly while nitrogen gas is passed through to remove all of the generated water. If no more water is generated, CaO of 8 grams is further added, the temperature is further increased up to 160° C., and $CO_2$ gas of 8-10 grams is introduced within 20 minutes. Then, all of the glycol is removed under vacuum with a distillation temperature up to 170° C. The mixture is cooled to about 100° C., and filtered with the added filter auxiliary, so that the clear overbased calcium salicylate is obtained, with sediment being below 0.05% by ASTM D2273, the viscosity at 100° C. being 40 cSt, the Total Base Number being 170, and the percentage of calcium is 6.1%.

EXAMPLE 2

The obtained nigger-brown and oil soluble alkyl salicylic acid without any solvent, which has a weight of 880 grams, is added to a reaction container containing base oil of 310 grams and CaO of 90 grams, and the mixture is heated up to 120° C. with stirring. Glycol of 125 grams is added to the mixture slowly while nitrogen gas is passed through to remove all of the generated water. If no more water is generated, CaO of 90 grams is further added, the temperature is further increased up to 160° C., and $CO_2$ gas of 40-45 grams is introduced within 20 minutes; then, CaO of 78 grams is added, and $CO_2$ gas of 35 grams is introduced within 20 minutes. Then, all of the glycol is removed under vacuum with a distillation temperature up to 170° C. The mixture is cooled to about 100° C., and filtered with the added filter auxiliary, so that the clear overbased calcium salicylate is obtained, with sediment being below 0.05% by ASTM D2273, the viscosity at 100° C. being 88 cSt, the Total Base Number being 305, and the percentage of calcium is 11.0%.

With the comparison with the overbased calcium salicylate prepared by other known methods, for example, the overbased calcium salicylate prepared with the use of methanol as a promoter, the product obtained in any of the above two Examples 1 and 2 contains little sediment by ASTM D2273 and a very low viscosity.

The high-temperature detergency and sediment controlling performance of the product prepared by the present invention is verified by a panel coker test which results in a carbon deposition no more than 20 milligrams, while the corresponding overbased sulphonate results in a carbon deposition more than 80 milligrams under the same verification conditions.

Various modifications may be made to the present invention without departing from the scope of the invention, which shall be defined by the attached claims.

It shall be understood that the above embodiments of the present invention are merely provided for describing the detailed constitution and process techniques of the invention. However, the invention is not limited to the above constitution and process techniques, that is, the implementation of the invention is note necessarily dependent upon the above detailed technique constitution and process. Any equivalent alternative of technical means or embodiment options are intended to fall into the scope of the invention, as understood by those skilled in the art.

The invention claimed is:

1. A process for producing an additive for lubricant oil that has a Total Base Number from about 100 to about 400, comprising overbasing reacting of components consisting of A, B, C, D and E at a temperature between 50° C. and 200° C., wherein, the component A is an alkyl salicylic acid that is of a particular molecular formula (I) before its neutralization or overbasing,

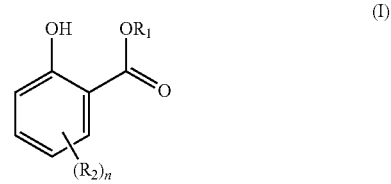

where $R_1$ represents a hydrogen, $R_2$ represents an alkyl group which has 10 to 50 carbon atoms, and n is 1 or 2;

the component B is CaO, which is added by one time or by plural times during the reaction;

the component C is ethylene glycol;

the component D is base oil; and the component E is carbon dioxide, which is introduced after the component B and is used each time when the component B is added;

the ethylene glycol is removed from the reacted mixture after the overbasing under vacuum, and then the reacted mixture is filtered to obtain a clear liquid product.

2. The process of claim 1, wherein, the ethylene glycol is added at a temperature between 50° C. and 180° C.

3. The process of claim 1, wherein, the amount of the introduced carbon dioxide is excessive for the CaO.

4. The process of claim 1, wherein the reacted mixture is filtered at a temperature below 170° C.

5. The process of claim 1, further comprising adding a filter auxiliary.

6. The process of claim 1, further comprising vacuum distillation of the product to remove partial flux oil for concentrating.

* * * * *